US012129333B2

(12) United States Patent
Moore

(10) Patent No.: US 12,129,333 B2
(45) Date of Patent: Oct. 29, 2024

(54) ORIENTED BIODEGRADABLE POLYURETHANES

(71) Applicant: POLYNOVO BIOMATERIALS PTY LIMITED, Port Melbourne (AU)

(72) Inventor: Timothy Graeme Moore, Port Melbourne (AU)

(73) Assignee: POLYNOVO BIOMATERIALS PTY LIMITED, Port Melbourne (AU)

( * ) Notice: Subject to any disclaimer, the term of this patent is extended or adjusted under 35 U.S.C. 154(b) by 633 days.

(21) Appl. No.: 17/416,691

(22) PCT Filed: Dec. 21, 2018

(86) PCT No.: PCT/AU2018/051389
§ 371 (c)(1),
(2) Date: Jun. 21, 2021

(87) PCT Pub. No.: WO2020/124120
PCT Pub. Date: Jun. 25, 2020

(65) Prior Publication Data
US 2022/0041793 A1    Feb. 10, 2022

(51) Int. Cl.
*C08G 18/42* (2006.01)
*C08G 18/10* (2006.01)
(Continued)

(52) U.S. Cl.
CPC ............. *C08G 18/73* (2013.01); *C08G 18/10* (2013.01); *C08G 18/222* (2013.01);
(Continued)

(58) Field of Classification Search
CPC ...... C08G 18/73; C08G 18/10; C08G 18/222; C08G 18/3206; C08G 18/4277; C08G 18/428; C08J 5/15
See application file for complete search history.

(56) References Cited

U.S. PATENT DOCUMENTS 4,123,589 A   10/1978  Korlatzki et al.
5,028,648 A    7/1991  Famili et al.
(Continued)

FOREIGN PATENT DOCUMENTS

JP    2001081152 A    3/2001
WO    2005089778 A1   9/2005
(Continued)

OTHER PUBLICATIONS

International Search Report and Written opinion issued on Mar. 28, 2019 for corresponding PCT Application No. PCT/AU2018/051389.
(Continued)

*Primary Examiner* — Michael L Leonard
(74) *Attorney, Agent, or Firm* — POLSINELLI PC

(57) ABSTRACT

Provided are oriented biodegradable thermoplastic polyurethane films. The films may be prepared by extruding and drawing biodegradable polyurethane films. The polyurethanes may be prepared from biodegradable polyols and/or biodegradable chain extenders. The films possess high tensile strength yet are degradable under biological conditions. The films may be utilized in the fabrication of devices, particularly implantable medical devices.

19 Claims, 4 Drawing Sheets

(51) Int. Cl.
*C08G 18/22* (2006.01)
*C08G 18/73* (2006.01)
*C08J 5/18* (2006.01)
*A61L 27/16* (2006.01)
*A61L 27/58* (2006.01)
*B29C 48/00* (2019.01)
*B29C 48/08* (2019.01)
*B29C 55/04* (2006.01)
*B29C 55/12* (2006.01)
*B29C 55/28* (2006.01)
*B29K 75/00* (2006.01)

(52) U.S. Cl.
CPC ....... *C08G 18/4277* (2013.01); *C08G 18/428* (2013.01); *C08J 5/18* (2013.01); *A61L 27/16* (2013.01); *A61L 27/58* (2013.01); *B29C 48/0018* (2019.02); *B29C 48/08* (2019.02); *B29C 55/04* (2013.01); *B29C 55/12* (2013.01); *B29C 55/28* (2013.01); *B29K 2075/00* (2013.01); *B29K 2995/0051* (2013.01); *B29K 2995/0053* (2013.01); *C08J 2375/06* (2013.01)

(56) References Cited

U.S. PATENT DOCUMENTS

| | | |
|---|---|---|
| 5,254,641 A | 10/1993 | Alex et al. |
| 5,775,779 A | 7/1998 | Abu-Isa et al. |
| 5,939,467 A | 8/1999 | Wnuk et al. |
| 6,013,340 A | 1/2000 | Bonk et al. |
| 7,964,696 B2 | 6/2011 | Gunatillake et al. |
| 8,343,472 B2 | 1/2013 | Adhikari et al. |
| 8,357,767 B2 | 1/2013 | Moore et al. |
| 8,445,581 B2 | 5/2013 | Gunatillake et al. |
| 8,729,202 B2 | 5/2014 | Mayadunne et al. |
| 9,034,378 B2 | 5/2015 | Moore et al. |
| 2007/0225387 A1 | 9/2007 | Mayadunne et al. |
| 2009/0099600 A1 | 4/2009 | Moore et al. |
| 2013/0131222 A1* | 5/2013 | Gross ............. C08G 18/36 528/80 |
| 2016/0195641 A1 | 7/2016 | Yang et al. |

FOREIGN PATENT DOCUMENTS

| | | |
|---|---|---|
| WO | 2007033418 A1 | 3/2007 |
| WO | 2019119057 A1 | 6/2019 |
| WO | 2019119060 A1 | 6/2019 |
| WO | 2019119061 A1 | 6/2019 |
| WO | 2020124120 A1 | 6/2020 |

OTHER PUBLICATIONS

Supplementary European Search Report and Written Opinion issued on Oct. 25, 2021 for corresponding European Application No. 18943413.

Wendels, Sophie et al: "Biobased polyurethanes for biomedical applications" Bioactive Materials, vol. 6, No. 4, Oct. 15, 2020, pp. 1083-1106 XP055854240.

* cited by examiner

ORIENTED BIODEGRADABLE POLYURETHANES

CROSS-REFERENCE TO RELATED APPLICATIONS

This application is a national stage application (under 35 U.S.C. § 371) of PCT/AU2018/051389, filed Dec. 21, 2018, which is incorporated herein by reference in its entirety.

FIELD

The present disclosure relates to oriented biodegradable thermoplastic polyurethane films. The films may be prepared by drawing biodegradable polyurethane films. The films possess high tensile strength and may be utilized in the fabrication of devices, particularly medical devices.

BACKGROUND

In recent years biodegradable polyurethanes have found increasing use in the fabrication of medical devices, particular devices which may be implanted in the human body.

Biodegradable polyurethanes may be designed so as to be biocompatible including biocompatibility of in vivo degradation products.

Biodegradable polyurethanes may be formulated using polyester polyols, aliphatic diisocyanates and diol chain extenders, such as ethylene glycol or 1,4-butanediol. The polyester polyol forms the 'soft' segment of the polymer while the diisocyanate and the chain extender together form the 'hard' segment. The hard segment provides ordered domains due to hydrogen bonding and imparts high mechanical strength to the polymer. The polyester polyol provides soft domains and imparts elastic properties to the polymer. Polyester polyols such as polycaprolactone, polyglycolide and polylactide are the most widely used polyols in biodegradable polyurethanes.

Biodegradation of these polymers occurs largely because of the hydrolytic degradation of the ester and urethane linkages in the polymer. In such polyurethanes, the soft segment degrades significantly faster than the hard segment. This is largely due to the presence of relatively easily hydrolysable ester linkages derived from the polyester polyol and the typically amorphous nature of the soft segment. The hard segment of biodegradable polyurethanes is formed from diisocyanates such as hexamethylene diisocyanate (HDI) or butane diisocyanate (BDI). The chain extender and the diisocyanate react to form urethane linkages in the hard segment of the polyurethane. The urethane linkages in the hard segment also degrade by hydrolysis, but at a significantly slower rate than ester linkages. Such polyurethanes degrade to low molecular weight products which are either bioresorbed or released through one of the waste disposal pathways in the body.

The use of conventional chain extenders such as ethylene glycol or 1,4-butanediol leads to polyurethane with hard segments comprising urethane functional groups. Because of the relatively slow degradation rates of these linkages compared with ester linkages, the polymer degradation may lead to oligomers containing mainly hard segments. This becomes a major concern, for certain applications of the polyurethanes, particularly when they are formulated with a higher percentage of hard segment (longer hard segment lengths). Accordingly, it is desirable if the hard segments also break down to low molecular weight compounds for rapid release from the body.

This has been addressed in, for example, International Patent Application Publication No. WO 2007/033418, by utilizing biodegradable chain extenders which have hydrolysable ester groups in their backbones. This provides polyurethanes in which the soft and hard segments may both be degradable under in vivo conditions.

Polyurethanes may be used in the form of thin films in the fabrication of medical devices and the strength of such films can be an important factor in device performance.

It would therefore be desirable to provide polyurethane films of high strength, yet which also are biodegradable under in vivo conditions. The present disclosure addresses this need.

The reference in this specification to any prior publication (or information derived from it), or to any matter which is known, is not, and should not be taken as an acknowledgement or admission or any form of suggestion that the prior publication (or information derived from it) or known matter forms part of the common general knowledge in the field of endeavour to which this specification relates.

SUMMARY

In one aspect the present disclosure provides an oriented biodegradable thermoplastic polyurethane film, said film being the extruded and drawn product of a biodegradable thermoplastic polyurethane.

In some embodiments the oriented biodegradable thermoplastic polyurethane film is biaxially oriented.

The oriented biodegradable thermoplastic polyurethane film may comprise polyurethane derived from one or more polyols, one or more diisocyanates and one or more chain extenders.

In some preferred embodiments the polyurethane is derived from one or more polyester polyols.

The chain extenders may be biodegradable or non-degradable. Preferably the chain extenders comprise biodegradable chain extenders.

As used herein, the term 'biodegradable' refers generally to the capability of being broken down in the normal functioning of living organisms/tissue, preferably into innocuous, non-toxic or biocompatible products.

Advantageously, the presently disclosed polyurethane films possess high strength. Orientation of the polyurethane film increase the tensile strength. The oriented polyurethane films may have an ultimate tensile strength of greater than 60 MPa, or greater than 70 MPa, or greater than 80 MPa, or greater than 90 MPa or greater than 100 MPa. In some preferred embodiments the oriented films have an ultimate tensile strength of greater than 100 MPa. In other preferred embodiments the oriented polyurethane film may have an ultimate tensile strength of greater than 150 MPa, or greater than 200 MPa. The ultimate tensile strength may be greater than 300 MPa or greater than 400 MPa.

Orientation of the film reduces the elongation at break.

Orientation of the film may result in a change in stress strain properties from plastic deformation to elastic deformation when under stress. This is advantageous for applications where permanent deformation of the material is not acceptable.

The oriented biodegradable thermoplastic polyurethane film may be dimensionally unstable, or substantially dimensionally unstable, to the application of stress. Stresses include physical stress and also the application of heat or exposure to a wet environment either in vivo or in vitro. This may be advantageous is applications such as, for example, shrink film.

The oriented biodegradable thermoplastic polyurethane film may display non-elastic behaviour.

In another aspect the present disclosure provides a method of making an oriented biodegradable thermoplastic polyurethane film comprising the step of extruding a biodegradable polyurethane as disclosed herein and drawing the extruded polyurethane in a single direction.

In another aspect the present disclosure provides a method of making an oriented biodegradable thermoplastic polyurethane film comprising the step of extruding a biodegradable polyurethane as disclosed herein and simultaneously drawing the extruded polyurethane in more than one direction.

Optionally, the oriented polyurethane film may be annealed after drawing. Annealing may provide dimensional stability to the oriented polyurethane.

Orientation of the polyurethane film decreases the thickness of the film. The oriented polyurethane film may have a thickness between about 20 μm and about 1000 μm, or between about 50 μm and about 500 μm, or between about 50 μm and about 400 μm. In some embodiments films of <20 μm thickness are envisaged.

The present disclosure further provides an annealed oriented biodegradable thermoplastic polyurethane film. The annealed film may be dimensionally stable, or substantially dimensionally stable, to the application of stress.

The annealed film may be elastic.

In another aspect the present disclosure provides an article of manufacture comprising an oriented biodegradable thermoplastic polyurethane film according to any one of the herein disclosed embodiments.

In another aspect the present disclosure provides a medical device comprising an oriented biodegradable thermoplastic polyurethane film according to any one of the herein disclosed embodiments.

In another aspect the present disclosure provides a medical implant comprising an orientated biodegradable thermoplastic polyurethane film according to any one of the herein disclosed embodiments.

In another aspect the present disclosure provided a laminate, said laminate comprising at least one layer comprising an orientated biodegradable thermoplastic polyurethane film according to any one of the herein disclosed embodiments.

At least one other layer may comprise one or more polymers. At least one other layer may comprise one or more polyurethanes. The one or more polyurethanes may be a foam.

In another aspect the present disclosure provides a shrink film comprising an oriented film according to one or more of the herein disclosed embodiments.

Other factors that influence the strength or properties of the oriented polyurethane film include, but are not limited to:
strength increases with molecular weight;
strength decreases if processed in the presence of moisture as the moisture can reduce the molecular weight;
moisture (softening of the material is often seen when soaked in water—can typically result in increased elongation and decreased modulus, and decreased ultimate tensile strength, and decrease in thermal transitions). This can result in a large change in stiffness (modulus) if water absorption causes the glass transition to drop below the testing temperature;
the presence of gels can result in premature failure of the material in tensile testing;
hard segment content, generally the higher the proportion of hard segment the higher the strength;
Position of the glass transition can affect the modulus; for the same material, a glass transition above testing temperature shows a higher modulus than a glass transition below the testing temperature.

The chain extenders may be represented by formula (1) or formula (2)

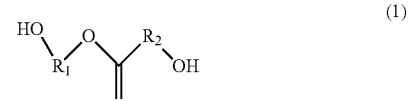

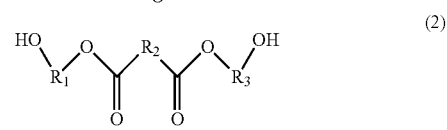

wherein $R_1$, $R_2$ and $R_3$ are independently selected from optionally substituted $C_{1-20}$ alkylene and optionally substituted $C_{2-20}$ alkenylene.

The polyurethane may have a number average molecular weight ($M_w$) up to 200,000 Daltons, or up to 150,000 Daltons, or up to 100,000 Daltons, or up to 60,000 Daltons, or up to 40,000 Daltons, or up to 20,000 Daltons.

The polyurethane may have a number average molecular weight ($M_w$) between 2,000 and 200,000 Daltons, or between 5,000 and 150,000 Daltons or between 10,000 and 100,000 Daltons or between 20,000 and 100,000 Daltons or between 2,000 and 60,000 Daltons, or between 2,000 and 40,000 Daltons or between 2,000 and 20,000 Daltons.

The polyurethane may have a number average molecular weight ($M_n$) up to 100,000 Daltons, or up to 75,000 Daltons, or up to 50,000 Daltons, or up to 30,000 Daltons, or up to 20,000 Daltons, or up to 10,000 Daltons. Preferably, the number average molecular weight of the polyurethane is between 50,000 and 100,000 Daltons.

The polyurethane may have a polydispersity ($M_w/M_n$) between 1.0 and 4.0, or between 1.0 and 3.5, or between 1.5 and 3.0. Preferably the polydispersity is between 1.0 and 2.0.

Polyols

The polyols may have a molecular weight between about 200 and about 2,000 Daltons, or between about 200 and about 1,500 Daltons, or between about 200 and about 1,300 Daltons.

The polyols may have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons.

The polyols may have a molecular weight of less than 500 Daltons or less than 400 Daltons or less than 350 Daltons, or less than 300 Daltons.

The polyols may be in the liquid state at 20° C. and atmospheric pressure. Alternatively, the polyols may be in the solid state at 20° C. and atmospheric pressure.

The polyols may be derived from one or more diol initiators and one or more hydroxy acids, diacids or cyclic esters and combinations thereof.

In one embodiment the polyol may be derived from one or more diol initiators and at least one hydroxy acid.

In one embodiment the polyol may be derived from one or more diol initiators and at least one diacid.

In one embodiment the polyol may be derived from one or more diol initiators and at least one cyclic ester.

In one embodiment the polyol may be derived from one or more diol initiators, at least one hydroxy acid and at least one diacid.

In one embodiment the polyol may be derived from one or more diol initiators, at least one hydroxy acid and at least one cyclic ester.

In one embodiment the polyol may be derived from one or more diol initiators, at least one diacid and at least one cyclic ester.

In one embodiment the polyol may be derived from one or more diol initiators, at least one hydroxyl acid, at least one diacid and at least one cyclic ester.

Non-limiting examples of the one or more diol initiators include ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of diacids include oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof. Non-limiting examples of hydroxy acids include l-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof. The polyols may be prepared via a ring-opening polymerisation reaction or a condensation reaction or via both a ring-opening polymerisation reaction and a condensation reaction.

Chain Extenders

In some embodiments R1, R2 and R3 of formulae (1) and (2) are independently selected from optionally substituted C1-6 alkylene and optionally substituted C2-6 alkenylene.

The term "optionally substituted" refers to a group which may or may not be further substituted with one or more groups selected from C1-6 alkyl, C2-6 alkenyl, C2-6 alkynyl, halo, halo C1-6 alkyl, halo C2-6 alkenyl, halo C2-6 alkynyl, hydroxy, C1-6 alkoxy, C2-6 alkenyloxy, halo C1-6 alkoxy, haloalkenyloxy, nitro, nitro C1-6 alkyl, nitro C2-6 alkenyl, nitro C-6 alkynyl, nitroheterocyclyl, amino, C1-6 alkylamino, C1-6 dialkylamino, C2-6 alkenylamino, C2-6 alkynylamino, acyl, alkenylacyl, alkynylacyl, acylamino, diacylamino, acyloxy, C1-6 alkylsulphonyloxy, heterocyclyl, heterocyclyloxy, heterocyclylamino, haloheterocyclyl, C1-6 alkylsulphenyl, carboalkoxy, mercapto, C1-6 alkylthio, acylthio, phosphorus-containing groups and the like. Preferred optional substituents are methyl, ethyl, propyl, butyl, and phenyl.

The chain extender of formula (1) or formula (2) is preferably hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol, and mixtures thereof.

The chain extender of formula (1) of formula (2) may be prepared from one or more diols and one or more hydroxy acids and/or cyclic esters.

Non-limiting examples of the one or more diols include ethylene glycol, 1,3-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof. Non-limiting examples of hydroxy acids include 1-lactic acid, d-lactic acid, d,l-lactic acid, mandelic acid, phenyl-lactic acid, hydroxybutyric acid, hydroxyvaleric acid or glycolic acid and combinations thereof. Non-limiting examples of cyclic esters include ε-caprolactone, glycolide, lactide, mandelide, and ρ-dioxanone and combinations thereof.

The polyurethane may further comprise one or more aliphatic polyol chain extenders which are hydrolytically non-degradable under in vivo conditions. For example, the polyurethane may further comprise one or more diol chain extenders which do not contain ester functionality in their backbones. Preferably, the non-degradable chain extender is an alkane diol having up to 30 carbon atoms, for example, ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and mixtures thereof.

Diisocyanates

The aliphatic diisocyanate is preferably 4,4'-methylene dicyclohexyl diisocyanate (HMDI), 1,6-hexane diisocyanate (HDI), 1,4-butane diisocyanate (BDI), L-lysine diisocyanate (LDI), ethyl-L-lysine diisocyanate (ELDI), methyl-L-lysine diisocyanate (MLDI), 2,4,4-trimethylhexamethylenediisocyanate, other similar diisocyanates, and mixtures thereof.

The degradation products from aliphatic isocyanates (such as ethyl lysine diisocyanate (ELDI)) are generally considered to be more biocompatible than the degradation products from aromatic diisocyanates. Accordingly, isocyanates such as hexamethylene diisocyanate (HDI) and ELDI may be particularly suitable. Isophorone diisocyanate (IPDI) may also be used. Combinations of isocyanates may be used and may in some instances be preferable—for example, glass transition can be adjusted by combinations of HDI and IPDI. Trimethylhexamethylenediisocyanate, 1,4-butane diisocyanate, methyl-lysine diisocyanate (MLDI) and other isocyanates commonly used in polyurethane synthesis may also be suitable.

Polyurethane Degradation

The polyurethane may contain hard and soft segments. The ratio of hard to soft segment influences the melting point of the polyurethane.

The hard segment content (% HS) of the polyurethane (that is, the combined content of the components derived from the chain extender of formula (1) or formula (2) and isocyanate, expressed by weight percentage) may range from 2 to 100 wt. %, or from 5 to 80 wt %, or from 10 to 70 wt %.

The soft segment content (% SS) of the polyurethane (that is, the percentage by weight of the components derived from the polyester polyol) may range from 5-98%, and in some embodiments, is at least 25% or at least 40%.

In some embodiments the polyurethane comprises hard and soft segments wherein the hard segment content (% HS) of the polyurethane is less than 60%, preferably between 30 and 60%.

The amount of chain extender of formula (1) or formula (2) in the polyurethane may be varied to vary the non-degradable length of continuous urethane in the hard segment. For example, the non-degradable length of the hard segment may be between a weight average molecular weight between 100 and 10,000 Daltons, or between 200 and 5,000 Daltons, or between 400 and 2,000 Daltons, or between 200 and 700 Daltons or between 320 and 700 Daltons.

The polyurethane may be in vivo degradable. The polyurethane may be degradable at temperatures between 35 and 42° C.

The polyurethane may degrade, under the conditions of ASTM F1635, such that the number average molecular weight ($M_n$) of the polyurethane decreases by between 10% and 90% in a period of one year or less.

Alternatively, the number average molecular weight ($M_n$) of the polyurethane may decrease by between 10% and 90% in a period of eleven months or less, or ten months or less, or nine months or less, or eight months or less, or seven months or less, or six months or less, or five months or less, or four months or less, or three months or less, or two months or less, or one month or less.

The rate of degradation, under the conditions of ASTM F1635, may be controlled through varying the nature and ratios of the components of the polyurethane. Accordingly, the polyurethane may be designed to degrade within a specific time period. This is advantageous in providing materials that are partially, fully, or substantially fully degradable in a specific time period, for example, when the functional aspects of the polyurethane are no longer required.

Melting Point

The melting point of the polyurethane may be between 60° C. and 190° C. The melting point may be between 60° C. and 180° C., or between 60° C. and 170° C., or between 60° C. and 160° C., or between 60° C. and 150° C., or between 60° C. and 140° C., or between 60° C. and 130° C., or between 60° C. and 120° C., or between 60° C. and 110° C., or between 60° C. and 100° C., or between 60° C. and 100° C., or between 60° C. and 90° C., or between 60° C. and 80° C., or between 60° C. and 70° C.

Where a clear melting transition occurs the melting point may be determined by differential scanning calorimetry. Other techniques know to those skilled in the art, such as dynamic mechanical thermal analysis, may also be utilised.

Further features and advantages of the present disclosure will be understood by reference to the following drawings and detailed description.

DESCRIPTION OF PREFERRED EMBODIMENTS

Figure 1:
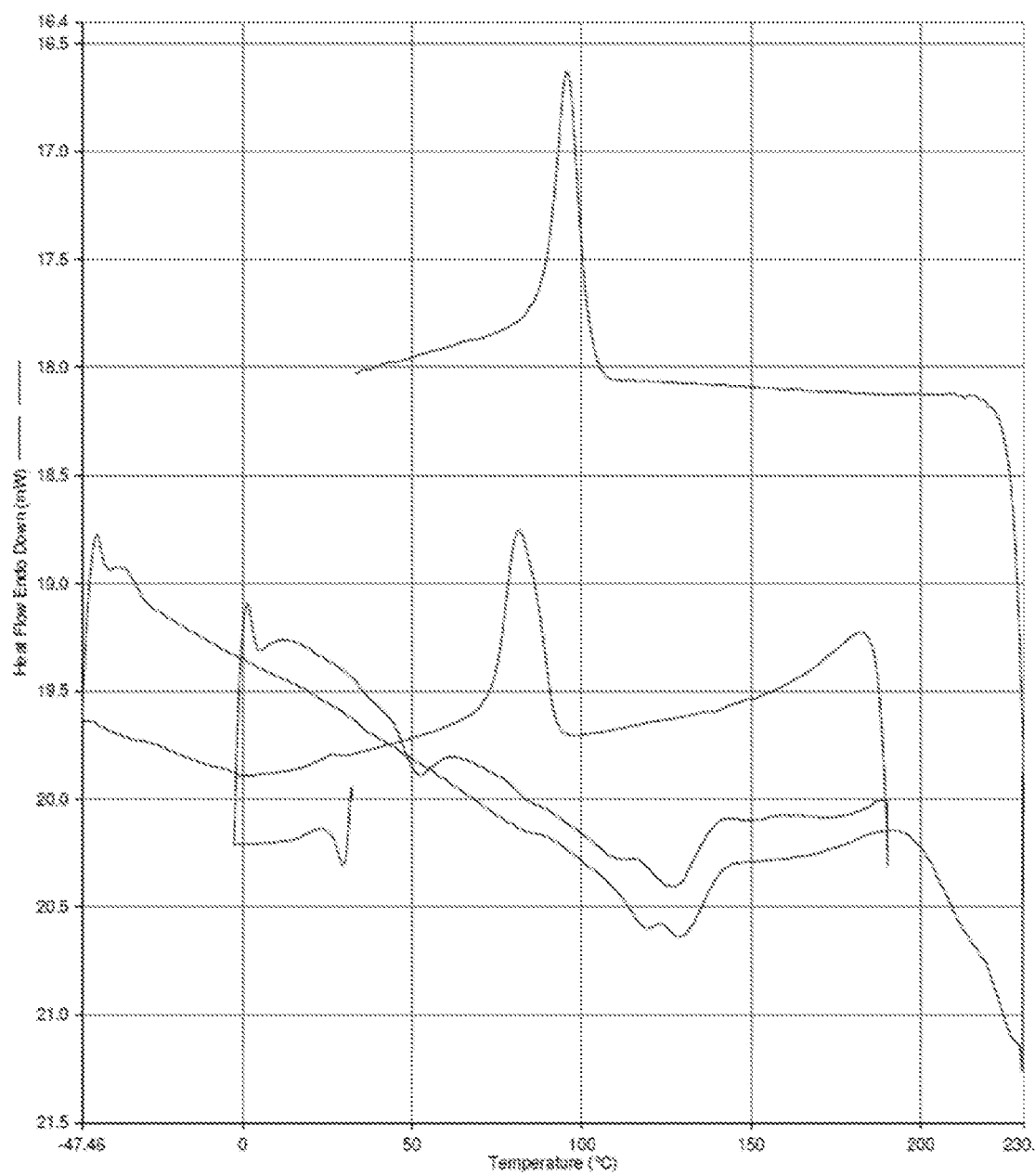
FIG. 1 shows the DSC of a comparative polyurethane, not according to the present disclosure.

The following is a detailed description of the disclosure provided to aid those skilled in the art in practicing the present disclosure. Those of ordinary skill in the art may make modifications and variations in the embodiments described herein without departing from the spirit or scope of the present disclosure.

Although any methods and materials similar or equivalent to those described herein can also be used in the practice or testing of the present disclosure, the preferred methods and materials are now described.

It must also be noted that, as used in the specification and the appended claims, the singular forms 'a', 'an' and 'the' include plural referents unless otherwise specified. Thus, for example, reference to 'chain extender' may include more than one chain extenders, and the like.

Throughout this specification, use of the terms 'comprises' or 'comprising' or grammatical variations thereon shall be taken to specify the presence of stated features, integers, steps or components but does not preclude the presence or addition of one or more other features, integers, steps, components or groups thereof not specifically mentioned.

Unless defined otherwise, all technical and scientific terms used herein have the meaning commonly understood by a person skilled in the art to which this disclosure belongs.

Unless specifically stated or obvious from context, as used herein, the term "about" is understood as within a range of normal tolerance in the art, for example within two standard deviations of the mean. 'About' can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein in the specification and the claim can be modified by the term 'about'.

Ranges provided herein are understood to be shorthand for all of the values within the range. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

The primary components and features used in the preparation of one or more embodiments of the polyurethane film as herein disclosed are discussed in detail in the following sections.

CERTAIN EMBODIMENTS

In one embodiment the present disclosure provides an oriented polyurethane film wherein the polyurethane is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol;
one or more aliphatic polyester polyols; and
one or more aliphatic diisocyanates;
wherein the polyurethane has a melting point between 60° C. and 190° C.; and
wherein the polyurethane degrades, under the conditions of ASTM F1635, such that the number average molecular weight ($M_n$) of the polyurethane decreases by between 10% and 90% in a period of one year or less.

In one embodiment the present disclosure provides an oriented polyurethane film wherein the polyurethane is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol;
one or more aliphatic polyester polyols; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethyl-hexamethylenediisocyanate;
wherein the polyurethane has a melting point between 60° C. and 190° C.; and
wherein the polyurethane degrades, under the conditions of ASTM F1635, such that the number average molecular weight ($M_n$) of the polyurethane decreases by between 10% and 90% in a period of one year or less.

In one embodiment the present disclosure provides an oriented polyurethane film wherein the polyurethane is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol; one or more aliphatic polyester polyols derived from one or more diol initiators and at least one hydroxy acid and/or cyclic ester; and
one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethyl-hexamethylenediisocyanate;
wherein the polyurethane has a melting point between 60° C. and 190° C.; and wherein the polyurethane degrades, under the conditions of ASTM F1635, such that the number average molecular weight ($M_n$) of the polyurethane decreases by between 10% and 90% in a period of one year or less.

In one embodiment the present disclosure provides an oriented polyurethane film wherein the polyurethane is derived from:
one or more chain extenders selected from hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol;
one or more aliphatic polyester polyols derived from one or more diol initiators and at least one hydroxy acid, diacid or cyclic ester, or combinations thereof, wherein the one or more diol initiators is selected from ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, and combinations thereof and wherein the at least one hydroxy acid is selected from 1-lactic acid, d-lactic acid, d,l-lactic acid, mandelic acid, phenyl-lactic acid, valeric acid or glycolic acid; wherein the one or more diacids is selected from oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and wherein the cyclic ester is selected from ε-caprolactone, glycolide, lactide, mandelide, and ρ-dioxanone; and one or more aliphatic diisocyanates selected from 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethyl-hexamethylenediisocyanate;
wherein the polyurethane has a melting point between 60° C. and 190° C.; and
wherein the polyurethane degrades, under the conditions of ASTM F1635, such that the number average molecular weight ($M_n$) of the polyurethane decreases by between 10% and 90% in a period of one year or less.

Bioactive Substances

Bioactive substances may optionally be added to the polyurethane. The bioactive substance may be formulated with the polyurethane before or after orientation.

Bioactive substances may be synthetic molecules, biomolecules, or multimolecular entities and include, but are not limited to, enzymes, organic catalysts, ribozymes, organometallics, proteins, glycoproteins, peptides, polyamino acids, antibodies, nucleic acids, steroidal molecules, antibiotics, silver, silver oxide, antivirals, antimycotics, anticancer agents, analgesic agents, antirejection agents, immunosuppressants, cytokines, carbohydrates, oleophobics, lipids, extracellular matrix and/or its individual components, demineralized bone matrix, hydroxyapatite, tricalcium phosphate, pharmaceuticals, chemotherapeutics, and therapeutics. Cells and non-cellular biological entities, such as viruses, virus vectors and prions can also be bioactive substances. The bioactive substances may be chemically bonded to the polyurethane.

The biological effect in humans or animals is for medical, therapeutic, cosmetic and veterinary purposes, and encompasses pharmaceuticals including drugs, cosmeceuticals, nutraceuticals, and nutritional agents. It will be appreciated that some of bioactive compounds can be classified in more than one of these classes.

A wide range of bioactive substances may be incorporated into the presently disclosed polyurethanes.

Examples include, but are not limited to, cardiovascular drugs, in particular antihypertensive agents (e.g. calcium channel blockers or calcium antagonists) and antiarrhythmic agents; congestive heart-failure pharmaceuticals; inotropic agents; vasodilators; ACE inhibitors; diuretics; carbonic anhydrase inhibitors; cardiac glycosides; phosphodiesterase inhibitors; α-blockers; β-blockers; sodium channel blockers; potassium channel blockers; β-adrenergic agonists; platelet inhibitors; angiotensin antagonists; anticoagulants; thrombolytic agents; treatments for bleeding; treatments for anaemia; thrombin inhibitors; antiparasitic agents; antibacterial agents; insulin; human growth hormone and peptides; vaccines; anti-inflammatory agents, in particular non-steroidal anti-inflammatory agents (NSAIDs), more particularly COX-2 inhibitors; steroidal anti-inflammatory agents; prophylactic anti-inflammatory agents; anti glaucoma agents; mast cell stabilisers; mydriatics; agents affecting the respiratory system; allergic rhinitis pharmaceuticals; α adrenergic agonists; corticosteroids; chronic obstructive pulmonary disease pharmaceuticals; xanthine-oxidase inhibitors; antiarthritis agents; gout treatments; autacoids and autacoid antagonists; anti mycobacterial agents; antifungal agents; antiprotozoal agents; anthelmintic agents; antiviral agents especially for respiratory, herpes, cyto-megalovirus, human immunodeficiency virus and hepatitis infections; treatments for leukaemia and Kaposi's sarcoma; pain management agents in particular opioids, anaesthetics and analgesics; neuroleptics; sympathomimetic pharmaceuticals; adrenergic agonists; drugs affecting neurotransmitter uptake or release;

anticholinergic pharmaceuticals; anti haemorrhoid treatments; agents to prevent or treat radiation or chemotherapeutic effects; lipogenesis drugs; fat reducing treatments; anti-obesity peptides; antiobesity agents such as lipase inhibitors; sympathomimetic agents; treatments for gastric ulcers and inflammation such as proton pump inhibitors; prostaglandins; VEGF inhibitors; antihyperlipidemic agents, in particular statins; drugs that affect the central nervous system (CNS) such as antipsychotic, antiepileptic and antiseizure drugs (anticonvulsants), psychoactive drugs, stimulants, antianxiety and hypnotic drugs, antidepressant drugs; anti Parkinson's pharmaceuticals; hormones and fragments thereof such as sex hormones; growth hormone antagonists; gonadotropin releasing hormones and analogues thereof; steroid hormones and their antagonists; selective estrogen modulators; growth factors; anti diabetic pharmaceuticals such as insulin, insulin fragments, insulin analogues, glucagon like peptides and hypoglycaemic agents; H1, H2, H3 and H4 antihistamines; peptide, protein, polypeptide, nucleic acids and oligonucleotide pharmaceuticals; analogues, fragments and variants of natural proteins, polypeptides, oligonucleotides and nucleic acids and such like compounds; agents used to treat migraine headaches; asthma pharmaceuticals; cholinergic antagonists; glucocorticoids; androgens; antiandrogens; inhibitors of adrenocorticoid biosynthesis; osteoporosis treatments such as biphosphonates; antithyroid pharmaceuticals; cytokine agonists; cytokine antagonists; anticancer drugs; antialzheimer drugs; HMG-CoA reductase inhibitors; fibrates; cholesterol absorption inhibitors; HDL cholesterol elevating agents; triglyceride reducing agents; anti-ageing or anti-wrinkle agents; precursor molecules for the generation of hormones; proteins such as collagen and elastin; antibacterial agents; anti acne agents; antioxidants; hair treatments and skin whitening agents; sunscreens, sun protectants and filters; variants of human apolipoprotein; precursor molecules for generation of hormones; proteins and peptides thereof; amino acids; plant extracts such as grape seed extract; DHEA; isoflavones; nutritional agents including vitamins, phytosterols and iridoid gylcosides, sesquiterpene lactones, terpenes, phenolic glycosides, triterpenes, hydroquinone derivatives, phenylalkanones; antioxidants such as retinol and other retinoids including retinoic acid and co enzyme Q10; omega-3-fatty acids; glucosamine; nucleic acids, oligonucleotides, antisense pharmaceuticals; enzymes; cytokines; cytokine analogues; cytokine agonists; cytokine antagonists; immunoglobulins; antibodies; antibody pharmaceuticals; gene therapies; lipoproteins; erythropoietin; vaccines; small and large molecule therapeutic agents for the treatment, or prevention of human and animal diseases such as allergy/asthma, arthritis, cancer, diabetes, growth impairment, cardiovascular diseases, inflammation, immunological disorders, baldness, pain, ophthalmological diseases, epilepsy, gynaecological disorders, CNS diseases, viral infections, bacterial infections, parasitic infections, GI diseases, obesity, and haemological diseases.

It is to be understood that pharmaceutically, nutraceutically or cosmeceutically acceptable derivatives of bioactive substances are included within the scope of the present disclosure.

The term "pharmaceutically, nutraceutically or cosmeceutically acceptable derivatives" includes, but is not limited to, pharmaceutically, nutraceutically or cosmeceutically acceptable salts, esters, salts of such esters, ethers, or any other derivative including prodrugs and metabolites, which upon administration to a subject (e.g. patient, human or animal) in need is capable of providing, directly or indirectly, a bioactive substance as otherwise described herein.

As used herein, the term "pharmaceutically, nutraceutically or cosmeceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio.

Pharmaceutically, nutraceutically or cosmeceutically acceptable salts are well known in the art. For example, S. M. Berge, et al. describe pharmaceutically, nutraceutically or cosmeceutically acceptable salts in detail in J. Pharmaceutical Sciences, 66:1-1 9, 1977.

Examples of pharmaceutically, nutraceutically or cosmeceutically acceptable nontoxic acid addition salts are salts of an amino group formed with inorganic acids such as hydrochloric acid, hydrobromic acid, phosphoric acid, sulfuric acid and perchloric acid or with organic acids such as—acetic-acid, oxalic acid, maleic acid, tartaric acid citric acid, succinic acid, or malonic acid or by using other methods used in the art such as ion exchange.

Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2 hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like.

Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate, and aryl sulfonate.

The term "pharmaceutically, nutraceutically or cosmeceutically acceptable ester" refers to esters which are hydrolysed in vivo and include those that break down readily in the human body to leave the parent compound or a salt thereof. Suitable ester groups include, for example, those derived from pharmaceutically, nutraceutically or cosmeceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of esters include formates, acetates, propionates, butyrates, acrylates and ethylsuccinates.

The term "pharmaceutically, nutraceutically or cosmeceutically acceptable prodrugs" as used herein includes those prodrugs of the biologically active substances which are, within the scope of sound medical judgment, suitable for use in contact with the tissues of a subject with undue toxicity, irritation, allergic response, and the like, commensurate with a reasonable benefit/risk ratio, and effective for their intended use, as well as the zwitterionic forms, where possible, of the biologically active substances.

The term "prodrug" refers to compounds that are rapidly transformed in vivo to yield a parent compound, for example by hydrolysis in blood. A thorough discussion is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987.

Degradation

In some embodiments the number average molecular weight ($M_n$) of the polyurethane may decrease by between 20% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 30% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 40% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 50% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 60% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 70% and 90% in a period of eleven months or less, or ten months or less, or nine months or less, or eight months or less, or seven months or less, or six months or less, or five months or less, or four months or less, or three months or less, or two months or less, or one month or less.

In some embodiments the number average molecular weight ($M_n$) of the polyurethane may decrease by between 80% and 90% in a period of eleven months or less, or ten months or less, or nine months or less, or eight months or less, or seven months or less, or six months or less, or five months or less, or four months or less, or three months or less, or two months or less, or one month or less.

EXAMPLES

General

Molecular weights were determined by gel permeation chromatography (GPC). Polyurethane tensile properties were measured using an Instron mechanical tester (model 5566).

EXAMPLE 1: POLYOL SYNTHESIS

Polyols were prepared by condensation of L-lactic acid (LLA), ε-caprolactone (CL) and 1,4-butane diol (BDO). All components were weighed into a glass reactor fitted with stirring, nitrogen outgassing, a condenser, and a heat source. The temperature was set to between 130° C. and 210° C. and the stirring and nitrogen flow started. Water was removed from the vessel via the condenser as the reaction proceeded. The reaction was continued until completion as indicated by residual acid measurement at which point the polyol was cooled and stored for use.

Polyols of weight average molecular weight 400 were prepared as above using weight ratios of LLA:CL of 30:70 along with BDO initiator.

EXAMPLE 2: BDO-CL CHAIN EXTENDER SYNTHESIS (6-HYDROXY-HEXANOIC ACID 4-HYDROXYBUTYL ESTER)

The chain extender was prepared by ring opening polymerisation of ε-caprolactone (CL) and 1,4-butane diol (BDO) in a 1:5 molar ratio. The temperature was set to between 130° C. and 210° C. with stirring and nitrogen. The reaction was continued until completion as indicated by gas chromatography (GC) analysis at which point the chain extender was cooled and stored for use.

EXAMPLE 3: POLYURETHANE SYNTHESIS (42% HARD SEGMENT)

Under nitrogen with stirring, 3 kg of the polyol of Example 1 was combined with HDI (1.734 kg). BDO-CL (Example 2; 63.5 g) and organozinc catalyst were added with heating to complete a prepolymer and the isocyanate content assayed. This was then chain extended using BDO (407.6 g) and further zinc catalyst. The stirred mixture was then poured into PTFE-lined trays and cured in an oven for 2 hours at 120° C. The cured polyurethane was then granulated.

EXAMPLE 4: POLYURETHANE SYNTHESIS (52% HARD SEGMENT)

Under nitrogen with stirring, 2.5 kg of the polyol of Example 1 was combined with HDI (1.9865 kg). BDO-CL (Example 2; 63.0 g) and organozinc catalyst were added with heating to complete a prepolymer and the isocyanate content assayed. This was then chain extended using BDO (619.3 g) and further zinc catalyst. The stirred mixture was then poured into PTFE-lined trays and cured in an oven for 2 hours at 120° C. The cured polyurethane was then granulated.

The polyurethanes of Examples 3 and 4 had respectively the following details:
  Polyol 400 Mw [BDO initiator-(LLA:CL, 30:70)], HDI, 42% HS, with 2 chain extenders: BDO and BDO-CL (degradable chain extender).
  Polyol 400 Mw [BDO initiator-(LLA:CL, 30:70)], HDI, 52% HS, with 2 chain extenders: BDO and BDO-CL (degradable chain extender).

EXAMPLE 5: CAST FILM (42% HS)

Dried granulated polyurethane (Example 3) was extruded on a small-scale cast film line equipped with extruder and chill rolls to provide a continuous film of between 235 and 420 μm thickness. Temperature during extrusion was between 160-185° C., with a lower temperature in the feeding zone.

EXAMPLE 6: STRETCHING—MACHINE DIRECTION ORIENTATION (MDO)

The cast film from Example 5 (300 µm thickness) was run through a continuous stretching machine (MDO) and stretched with heat (from 40° C. to 90° C.). Stretch ratios of up to 1:5.5 were used and the measured residual stretching ratios were between 1:2.3 and 1:4. The stretching was conducted in two manners—using a roll of pre-prepared cast film, and also in series with the immediate output of the cast film line being fed into the continuous stretcher as a continuous process. The film was collected on separate rolls for each condition.

EXAMPLE 7: RELAXATION OF THE STRETCHED CAST FILM

The stretched material (of example 6) was annealed (60-70° C.) and the shrinkage due to relaxation measured. All the stretched materials shrank from 15 cm in length (machine direction) to between 9.4 and 10.7 cm in length (a decrease in length of approximately one third). The unstretched material (cast film) did not shrink at all.

EXAMPLE 8: PROPERTIES OF CAST FILM (NON-ORIENTED 42% HS POLYURETHANE FILM)

The 300 µm thick extruded polymer of Example 5 was cut in the machine direction to strips of 10 mm width and 21 cm length, and tensile-tested on the Instron model 5566 with fibre grips, a 50 mm gauge length, 500 mm/min, and no extensometer. The average ultimate tensile stress was 56.2 MPa, and the elongation at break was 1208%. Thermal properties were assessed by DSC (Perkin-Elmer). FIG. 1 shows the DSC of the 42% HS polyurethane (unstretched).

EXAMPLE 9: PROPERTIES OF STRETCHED CAST FILM (ORIENTED 42% HS POLYURETHANE FILM)

The 300 µm continuous film was stretched at room temperature by hand to provide oriented specimens of 110-140 µm thickness. Strips were tensile-tested on the Instron model 5566 with fibre grips, a 50 mm gauge length, 500 mm/min, and no extensometer. The average ultimate tensile stress was 118.2 MPa, and the elongation at break was 334%.

The ultimate tensile stress was much higher for the oriented material but the elongation at break was lower (compared with the unoriented material).

EXAMPLE 10: MELT PRESSING POLYMER FILM

Granulated polymer of Example 3 (42% HS) was heated above the melting point and pressed on a Carver press at up to 10 tons pressure between glass fibre-reinforced PTFE. The pressed polymer was removed and cooled before removing from the PTFE sheets. The resulting polymer sheets were typically about 20 cm in diameter and between about 100-200 microns in thickness. Film thickness and diameter can be varied by the amount of polymer, the temperature, and the pressure.

EXAMPLE 11: BIAXIALLY-ORIENTED FILM

Melt-pressed polymer of Example 10 (42% HS) was stretched simultaneously in two directions (3:1, 65° C.) on a lab stretcher with heat to provide a biaxially-oriented film of 60-80 µm thickness. Strips were cut of 10 mm width, 21 cm length, and tensile-tested on the Instron model 5566 with fibre grips, a 50 mm gauge length, 500 mm/min, and no extensometer. The maximum ultimate tensile stress was 100.0 MPa, and the elongation at break was 391%. A piece of the stretched film was annealed and showed shrinkage from 10 cm×10 cm to 8.2 cm×8.3 cm (100-120 µm).

EXAMPLE 12: TENSILE PROPERTIES FOR AN UNORIENTED FILM

Specimens of 5 mm width were prepared from Example 10 and tested on Instron model 5566 at 500 mm/min and gauge length of 50 mm, using fibre grips without an extensometer. Stress at yield (9.6 MPa), UTS (37.6 MPa), elongation at break (998%).

Figure 2:
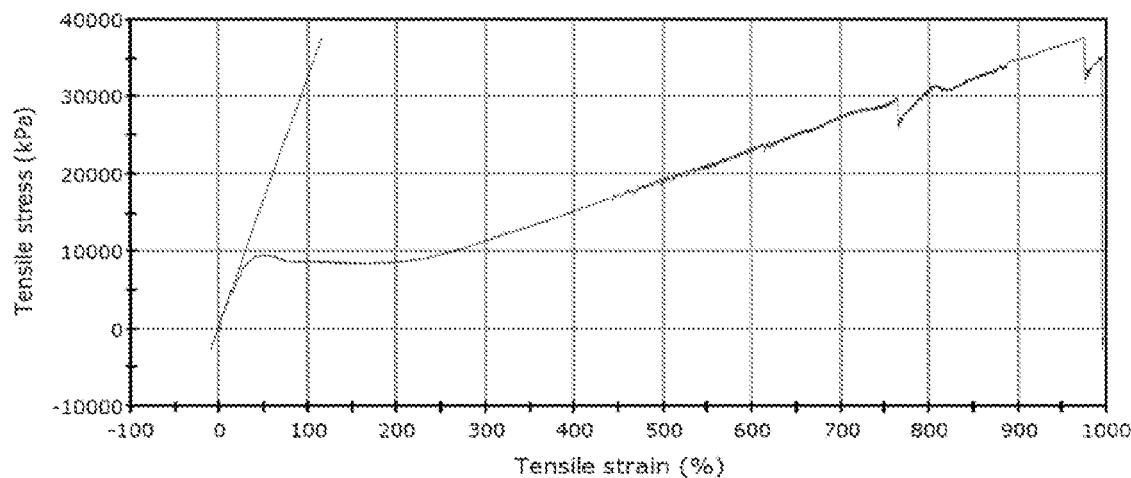
FIG. 2 shows the stress strain curve of a comparative polyurethane, not according to the present disclosure.

FIG. 2 shows a stress-strain curve for an unoriented material. There is a yield point at approximately 50% elongation where the material necks, then it draws until about 200-250% elongation, and then the stress increases. This behaviour suggests a plastic material (cold-drawing), rather than elastic.

EXAMPLE 13: EXAMPLE OF AN ORIENTED POLYMER

A 5 mm strip of polymer of Example 10 was stretched by hand. It stretched uniformly and remained in the stretched condition after releasing tension. The stretched material was tested on the Instron model 5566 using fibre grips without extensometer at 500 mm/min and gauge length of 50 mm. A yield point was not evident, UTS (125.4 MPa), elongation (219%).

Figure 3:
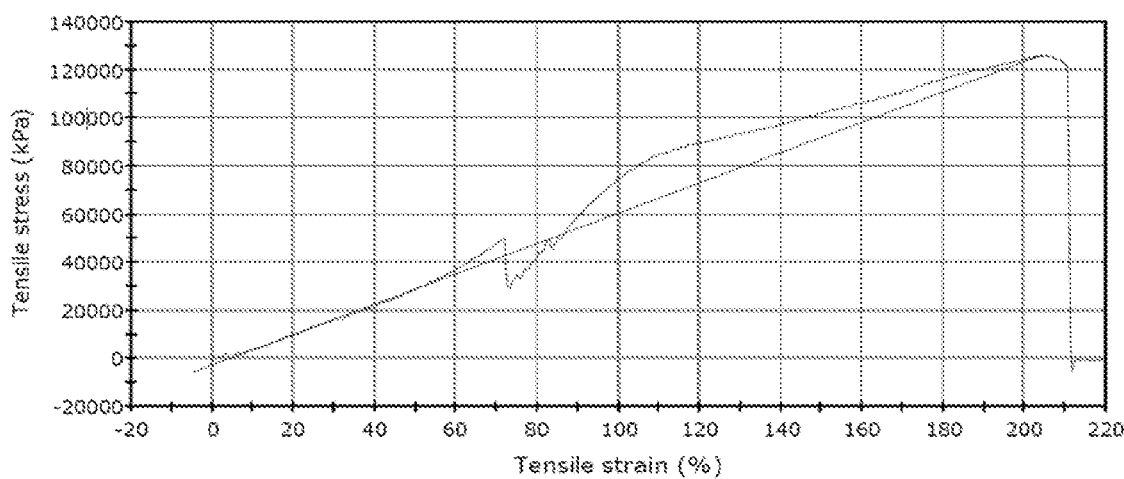
FIG. 3 shows the stress strain curve of a polyurethane according to one embodiment of the present disclosure.

FIG. 3 shows a stress-strain curve of the stretched material which illustrates greatly increased tensile strength post-stretching, and an elastic stress-strain curve.

EXAMPLE 14: EFFECT OF ANNEALING THE STRETCHED POLYMER

A 5 mm strip of the polymer of Example 10 was prepared and marked with a 10 cm interval, then stretched by hand and re-measured the interval to be 35 cm. It stretched uniformly and remained in the stretched condition after releasing tension. The polymer sample was placed in the oven at 70° C. to anneal for 60 seconds and re-measured the interval to be 25 cm (contracted 10 cm). The final annealed material was tested on the Instron model 5566 using fibre grips without extensometer at 500 mm/min and gauge length of 50 mm. Yield point was not evident, UTS (101.5 MPa), elongation (312%).

Figure 4:
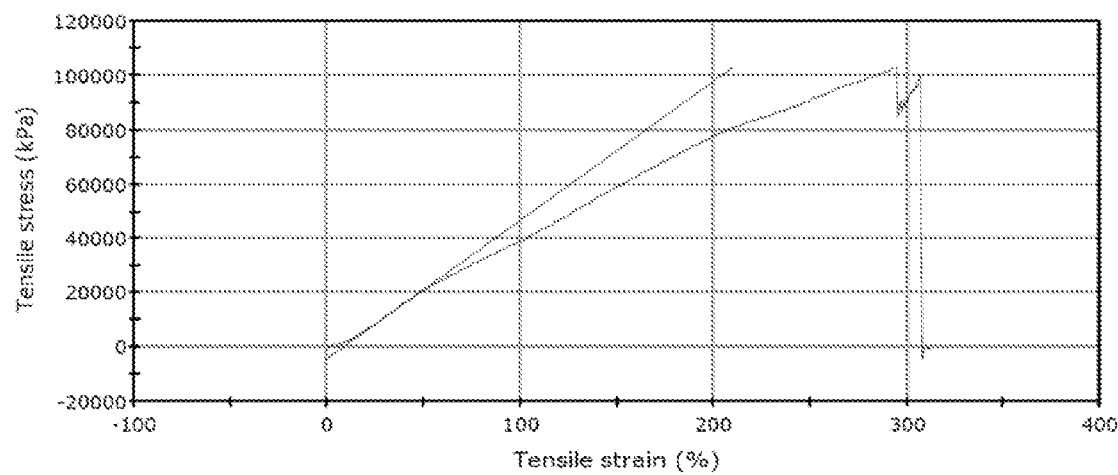
FIG. 4 shows the stress strain curve of a polyurethane according to one embodiment of the present disclosure.

FIG. 4 shows an Example of a stress-strain curve for a stretched and annealed material. It can be seen that the material has a higher tensile strength than the unoriented material, and exhibits no yield point indicating elastic behaviour.

EXAMPLE 15: PERMANENT DEFORMATION FOR AN UNSTRETCHED MATERIAL

A 5 mm strip of polymer of Example 10 was marked with a 19.3 mm interval, then tested on the Instron model 5566 using fibre grips without extensometer at 500 mm/min and gauge length of 50 mm, and a stop condition of 15 MPa tensile stress. The specimen elongated until the stress reached 15 MPa (420% elongation), then the specimen was removed and the interval re-measured. The interval was re-measured to be 48 mm in length (over double the length) and remained in the elongated state.

Figure 5:
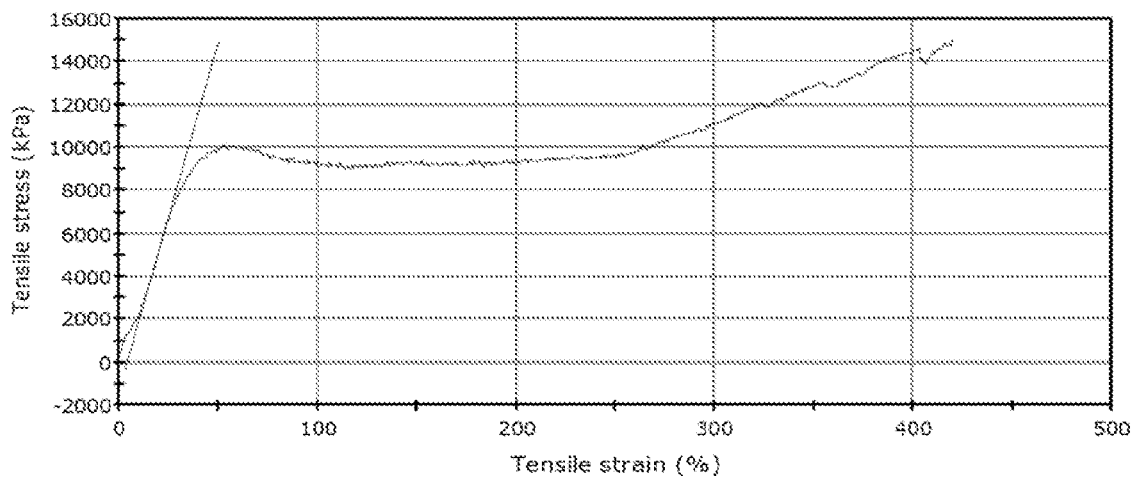
FIG. 5 shows the stress strain curve of a comparative polyurethane, not according to the present disclosure.

FIG. 5 shows an example of a stress strain curve for an unoriented material stopping at 15 MPa stress.

EXAMPLE 16: ELASTICITY OF AN ORIENTED MATERIAL

A 5 mm strip of polymer of Example 10 was stretched by hand past the yield point until the entire sample had drawn down and was even. A 14.2 mm interval was marked and the specimen tested on the Instron model 5566 using fibre grips without extensometer at 500 mm/min and gauge length of 50 mm, and a stop condition of 15 MPa tensile stress. The specimen elongated until the stress reached 15 MPa (32% elongation), then the specimen was removed and the interval re-measured. The interval was re-measured to be unchanged after testing.

Figure 6:
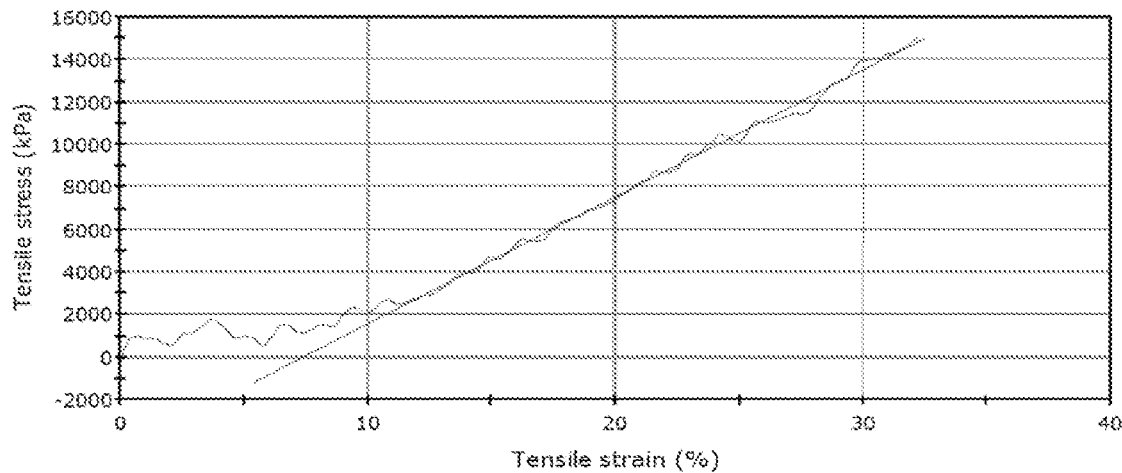
FIG. 6 shows the stress strain curve of a polyurethane according to one embodiment of the present disclosure.

FIG. 6 shows an Example of a stress-strain curve for a stretched material, stopping at 15 MPa stress.

EXAMPLE 17: ELASTICITY OF AN ORIENTED AND ANNEALED MATERIAL

A 5 mm strip of polymer of Example 10 was stretched by hand past the yield point until the entire sample had drawn down and was even, then annealed the specimen for one minute at 70° C., then marked a 15.3 mm interval and tested the specimen on the Instron model 5566 using fibre grips without extensometer at 500 mm/min and gauge length of 50 mm, and a stop condition of 15 MPa tensile stress. The specimen elongated until the stress reached 15 MPa (34% elongation), then the specimen was removed and the interval re-measured. The interval was re-measured to be unchanged after testing.

Figure 7:
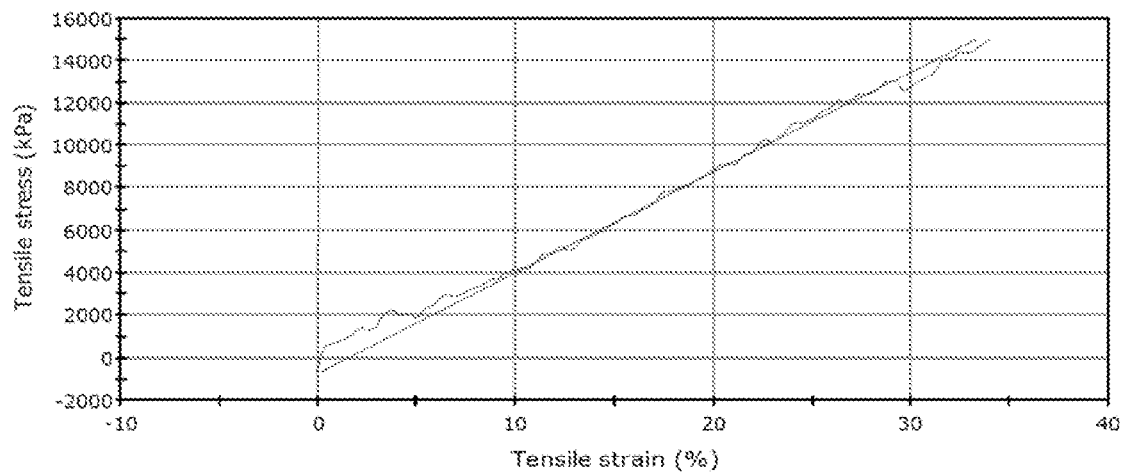
FIG. 7 shows the stress strain curve of a polyurethane according to one embodiment of the present disclosure.

FIG. 7 shows an Example of a stress-strain curve for a stretched and annealed material, stopping at 15 MPa stress.

EXAMPLE 18: 52% HS STRETCHING

Polymer granulate of Example 4 was extruded (Thermo-Electron Prism) at 190° C. into a 3 mm filament and collected. A 10 cm interval was measured and then the filament was stretched at room temperature by hand and the interval re-measured to be 21.8 cm. Initial thickness and final thickness (post-stretching) were 3.07 mm and 1.96 mm respectively.

EXAMPLE 19: INFLUENCE OF ANNEALING

Two sheets of cast film, prepared as in Example 5, were stretched 2.4 times in each direction and one was annealed for 60 seconds at 65° C. The non-annealed material shrank with heat (~65° C. in water) by 20% in the length and width (from 10 cm to 8 cm in each direction), however the annealed material only shrank by 5% under the same conditions (from 10.0 cm to 9.5 cm in both directions).

The contents of all references, and published patents and patent applications cited throughout the application are hereby incorporated by reference. Those skilled in the art will recognize that the disclosure may be practiced with variations on the disclosed structures, materials, compositions and methods, and such variations are regarded as within the ambit of the disclosure.

Those skilled in the art will recognize, or be able to ascertain using no more than routine experimentation, many equivalents to the specific embodiments and methods described herein. Such equivalents are intended to be encompassed by the scope of the following claims.

It is understood that the detailed examples and embodiments described herein are given by way of example for illustrative purposes only, and are in no way considered to be limiting to the disclosure. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the disclosure described herein. Such equivalents are intended to be encompassed by the following claims.

The invention claimed is:

1. An oriented biodegradable thermoplastic polyurethane film, said film being the extruded and drawn product of a biodegradable thermoplastic polyurethane, wherein:
   the film is biaxially oriented;
   the polyurethane comprises hard and soft segments;
   the hard segment content (% HS) of the polyurethane is less than 60 wt %; and
   the polyurethane is derived from:
      one or more aliphatic polyester polyols;
      one or more aliphatic isocyanates; and
      one or more biodegradable chain extenders represented by formula (1) or formula (2):

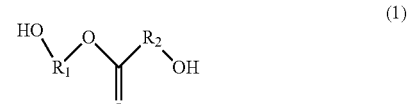

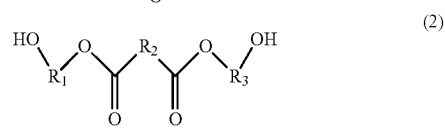

wherein R1, R2 and R3 are independently selected from optionally substituted $C_{1-20}$ alkylene and optionally substituted $C_{2-20}$ alkenylene.

2. An oriented biodegradable thermoplastic polyurethane film according to claim 1, wherein the polyester polyol is derived from one or more diol initiators and one or more hydroxy acids, diacids or cyclic esters and combinations thereof.

3. An oriented biodegradable thermoplastic polyurethane film according to claim 1, wherein one or more of the following applies:
   the polyols have a molecular weight between about 200 and about 2,000 Daltons, or between about 200 and about 1,500 Daltons, or between about 200 and about 1,300 Daltons;
   the polyols have a molecular weight of less than or equal to about 10,000 Daltons, or less than or equal to about 8,000 Daltons, or less than or equal to about 6,000 Daltons, or less than or equal to about 4,000 Daltons, or less than or equal to about 2,000 Daltons, or less than or equal to about 1,500 Daltons, or less than or equal to about 1,000 Daltons, or less than or equal to about 800 Daltons, or less than or equal to about 600 Daltons, or less than or equal to about 500 Daltons, or less than or equal to about 400 Daltons, or less than or equal to about 350 Daltons, or less than or equal to about 300 Daltons; or the polyols have a molecular weight of less than 500 Daltons or less than 400 Daltons or less than 350 Daltons, or less than 300 Daltons.

4. An oriented biodegradable thermoplastic polyurethane film according to claim 1, wherein $R_1$, $R_2$ and $R_3$ of formulae (1) and (2) are independently selected from optionally substituted $C_{1-6}$ alkylene and optionally substituted $C_{2-6}$ alkenylene.

5. An oriented biodegradable thermoplastic polyurethane film according to claim 2, wherein one or more of the following applies:
the one or more diol initiators are selected from the group consisting of ethylene glycol, 1,3-propanediol, 1,2-propanediol, 1,4-butanediol, pentanediol, hexamethylenediol, heptanediol, octanediol, nonanediol, decanediol, dodecanediol, 2-ethyl-1,3-hexanediol (EHD), 2,2,4-trimethyl pentane-1,3-diol (TMPD), 1,4-cyclohexane dimethanol, diethylene glycol, dipropylene glycol, and combinations thereof;
the diacids are selected from the group consisting of oxalic acid, malonic acid, succinic acid, glutaric acid, adipic acid, pimelic acid, suberic acid, azelaic acid, sebacic acid, undecanedioic acid, dodecanedioic acid, tridecanedioic acid, and hexadecanedioic acid and combinations thereof;
the hydroxy acids are selected from the group consisting of l-lactic acid, d-lactic acid, d,l-lactic acid, mandelic acid, phenyl-lactic acid, hydroxybutyric acid, hydroxyvaleric acid or glycolic acid and combinations thereof; or
the cyclic esters are selected from the group consisting of ε-caprolactone, glycolide, lactide, mandelide, and ρ-dioxanone and combinations thereof.

6. An oriented biodegradable thermoplastic polyurethane film according to claim 1, wherein the isocyanate is an aliphatic diisocyanate selected from the group consisting of 4,4'-methylene dicylcohexyl diisocyanate (HMDI), 1,6-hexane diisocyanate (HDI), 1,4-butane diisocyanate (BDI), L-lysine diisocyanate (LDI), 2,4,4-trimethylhexamethylenediisocyanate, ethyl-L-lysine diisocyanate (ELDI), methyl-L-lysine diisocyanate (MLDI), and mixtures thereof.

7. An oriented biodegradable thermoplastic polyurethane film according to claim 1, wherein the polyurethane further comprises one or more aliphatic polyol chain extenders which are hydrolytically non-degradable under in vivo conditions.

8. An oriented biodegradable thermoplastic polyurethane film according to claim 1, wherein one or more of the following applies:
the polyurethane has a melting point between 45° C. and 190° C.;
the polyurethane has a number average molecular weight ($M_w$) up to 200,000 Daltons, or up to 150,000 Daltons, or up to 100,000 Daltons, or up to 60,000 Daltons, or up to 40,000 Daltons, or up to 20,000 Daltons;
the polyurethane has a number average molecular weight ($M_w$) between 2,000 and 200,000 Daltons, or between 5,000 and 150,000 Daltons or between 10,000 and 100,000 Daltons or between 20,000 and 100,000 Daltons or between 2,000 and 60,000 Daltons, or between 2,000 and 40,000 Daltons or between 2,000 and 20,000 Daltons; or
the polyurethane has a polydispersity ($M_w/M_n$) between 1.0 and 4.0, or between 1.0 and 3.5, or between 1.5 and 3.0, or between 1.0 and 2.0.

9. An oriented biodegradable thermoplastic polyurethane film according to claim 1, wherein one or more of the following applies:
the hard segment content (% HS) of the polyurethane is between 30 to 60%; or
the non-degradable length of the hard segment is between a weight average molecular weight between 100 and 10,000 Daltons, or between 200 and 5,000 Daltons, or between 400 and 2,000 Daltons, or between 200 and 1,000 Daltons or between 200 and 700 Daltons, or between 320 and 700 Daltons.

10. An oriented biodegradable thermoplastic polyurethane film according to claim 1, wherein one or more of the following applies:
the film has an ultimate tensile strength of greater than 60 MPa, or greater than 70 MPa, or greater than 80 MPa, or greater than 90 MPa or greater than 100 MPa; or
wherein the film has an ultimate tensile strength of greater than 150 MPa, or greater than 200 MPa, or greater than 250 MPa, or greater than 300 MPa, or greater than 400 MPa.

11. An oriented biodegradable thermoplastic polyurethane film according to claim 1, wherein the film is dimensionally unstable, or substantially dimensionally unstable, to the application of stress.

12. An oriented biodegradable thermoplastic polyurethane film according to claim 1, wherein the film is annealed.

13. An oriented biodegradable thermoplastic polyurethane film according to claim 1, wherein the film is dimensionally stable, or substantially dimensionally stable, to the application of stress.

14. An oriented biodegradable thermoplastic polyurethane film according to claim 1, wherein the film is elastic.

15. A medical device or implant comprising an oriented biodegradable thermoplastic polyurethane film according to claim 1.

16. A laminate, said laminate comprising at least one layer comprising an orientated biodegradable thermoplastic polyurethane film according to claim 1.

17. An oriented biodegradable thermoplastic polyurethane film according to claim 1, wherein the chain extender of formula (1) or formula (2) is selected from the group consisting of hydroxy-acetic acid 3-hydroxy-propyl ester, 6-hydroxy-hexanoic acid 2-hydroxyethyl ester, 6-hydroxy-hexanoic acid 4-hydroxybutyl ester, ethylene glycol succinic acid diester diol and ethylene glycol fumaric acid diester diol, and mixtures thereof.

18. An oriented biodegradable thermoplastic polyurethane film according to claim 7, wherein the aliphatic polyol chain extenders do not contain ester functionality in their backbones; or the one or more aliphatic polyol chain extenders is an alkane diol having up to 30 carbon atoms.

19. An oriented biodegradable thermoplastic polyurethane film according to claim 18, wherein the alkane diol is ethylene glycol, 1,3-propanediol, 1,2-propanediol, 1,4-butanediol, pentanediol, hexamethylenediol, heptanediol, nonanediol, dodecanediol, 2-ethyl-1,3-hexanediol (EHD), 2,2,4-trimethyl pentane-1,3-diol (TMPD), 1,6-hexanediol, 1,4-cyclohexane dimethanol, diethylene glycol, dipropylene glycol, or mixtures thereof.

* * * * *